(12) United States Patent
Abrams et al.

(10) Patent No.: US 12,029,870 B2
(45) Date of Patent: Jul. 9, 2024

(54) MEDICAL DEVICE HAVING NON-FILTERED CSF WITHDRAWAL PATHWAY

(71) Applicant: CEREBRAL THERAPEUTICS, INC., Aurora, CO (US)

(72) Inventors: Daniel J. Abrams, Denver, CO (US); Lisa Lynn Shafer, Stillwater, MN (US)

(73) Assignee: CEREBRAL THERAPEUTICS, INC., Aurora, CO (US)

( * ) Notice: Subject to any disclaimer, the term of this patent is extended or adjusted under 35 U.S.C. 154(b) by 181 days.

(21) Appl. No.: 17/376,589

(22) Filed: Jul. 15, 2021

(65) Prior Publication Data
US 2022/0016403 A1 Jan. 20, 2022

Related U.S. Application Data

(60) Provisional application No. 63/209,835, filed on Jun. 11, 2021, provisional application No. 63/052,284, filed on Jul. 15, 2020.

(51) Int. Cl.
*A61M 27/00* (2006.01)
*A61M 5/142* (2006.01)
(Continued)

(52) U.S. Cl.
CPC ...... *A61M 27/006* (2013.01); *A61M 5/14276* (2013.01); *A61M 5/158* (2013.01);
(Continued)

(58) Field of Classification Search
CPC .. A61B 2010/0077; A61M 2025/0037; A61M 2039/0264; A61M 2005/14284;
(Continued)

(56) References Cited

U.S. PATENT DOCUMENTS

| 5,897,528 A | 4/1999 | Schultz |
| 2007/0255237 A1* | 11/2007 | Lobl ............... A61M 39/105 604/288.01 |

(Continued)

FOREIGN PATENT DOCUMENTS

| EP | 0904119 | 3/1999 |
| EP | 0995460 | 4/2022 |

(Continued)

OTHER PUBLICATIONS

International Search Report and Written Opinion from PCT App. No. PCT/US2021/041772 dated Nov. 17, 2021, 14 pages.
(Continued)

*Primary Examiner* — Brandy S Lee
(74) *Attorney, Agent, or Firm* — Mueting Raasch Group (57) ABSTRACT

An implantable medical device for delivering therapeutic fluid to, and withdrawing cerebrospinal fluid (CSF) from, a CSF-containing space, includes a first inlet configured to be accessed by a needle of an aspiration device; a first outlet; a first fluid pathway extending from the first inlet to the first outlet; a second inlet; a second outlet; and a second fluid pathway extending from the second inlet to the second outlet. The first fluid pathway is free of a filter configured to prevent passage of a microbe.

11 Claims, 6 Drawing Sheets

(51) Int. Cl.
*A61M 5/158* (2006.01)
*A61M 5/165* (2006.01)
*A61M 39/02* (2006.01)
*A61B 10/00* (2006.01)
*A61M 5/14* (2006.01)
*A61M 25/00* (2006.01)

(52) U.S. Cl.
CPC ........ *A61M 5/165* (2013.01); *A61M 39/0208* (2013.01); *A61M 39/0247* (2013.01); *A61B 2010/0077* (2013.01); *A61M 5/1408* (2013.01); *A61M 2005/14284* (2013.01); *A61M 2025/0037* (2013.01); *A61M 2039/025* (2013.01); *A61M 2039/0264* (2013.01); *A61M 2210/0687* (2013.01); *A61M 2210/0693* (2013.01)

(58) Field of Classification Search
CPC ........ A61M 27/006; A61M 2210/0687; A61M 2210/0693; A61M 39/0208; A61M 5/14276; A61M 5/158; A61M 5/165
See application file for complete search history.

(56) References Cited

U.S. PATENT DOCUMENTS

| | | |
|---|---|---|
| 2008/0058476 A1 | 3/2008 | Whiteker et al. |
| 2015/0367067 A1 | 12/2015 | Minaie et al. |
| 2017/0173267 A1 | 6/2017 | Ashmead et al. |
| 2018/0028746 A1 | 2/2018 | Abrams et al. |
| 2018/0140810 A1 | 5/2018 | Cataltepe |
| 2019/0151239 A1 | 5/2019 | Abrams et al. |
| 2020/0338325 A1 | 10/2020 | Shachar et al. |
| 2021/0077714 A1 | 3/2021 | Bodner |
| 2021/0100990 A1 | 4/2021 | Yoo et al. |
| 2021/0252266 A1 | 8/2021 | Otto |

FOREIGN PATENT DOCUMENTS

| | | |
|---|---|---|
| WO | 1996/033761 | 10/1996 |
| WO | 2008/141321 | 11/2008 |
| WO | 2018/023041 | 2/2018 |

OTHER PUBLICATIONS

Written Opinion from PCT App. No. PCT/US2021/041772 dated May 30, 2022, 8 pages.

Leontariti et al., "Circulating miR-146a and miR-134 in predicting drug-resistant epilepsy in patients with focal impaired awareness seizures" May 2020 Epilepsia, 61(5):959-970.

Lubrizol Corporation, webinar, "Materials for Implantable Devices: Decoding Thermoplastic Polyurethanes" copyright 2022. Available on the world wide web at: lubrizol.com/Health/Medical/Resource-Hub/Webinars/Materials-for-Implantable-Devices-Decoding-Thermoplastic-Polyurethanes, 1 page.

* cited by examiner

MEDICAL DEVICE HAVING NON-FILTERED CSF WITHDRAWAL PATHWAY

RELATED APPLICATIONS

This application claims the benefit of U.S. Provisional Patent Application No. 63/052,284, filed on Jul. 15, 2020, and U.S. Provisional Patent Application No. 63/209,835, filed on Jun. 11, 2021, which provisional patent applications are hereby incorporated herein by reference in their respective entireties to the extent that they do not conflict with the disclosure presented herein.

FIELD

The present disclosure relates to, among other things, implantable medical devices, such as devices for delivering fluid to cerebrospinal fluid (CSF) containing space, withdrawing fluid from a CSF-containing space, or delivering fluid to a CSF-containing space and withdrawing fluid from a CSF-containing space.

INTRODUCTION

Delivery of therapeutic agents to the brain and treatment of diseases of the brain present challenges. For example, many therapeutic agents are not able to reach the brain at therapeutic concentrations when administered through traditional routes due to the blood-brain-barrier (BBB). In addition, systemic concentrations of therapeutic agents, or metabolites or degradation products thereof, may be undesirably high to achieve therapeutic levels in the brain when therapeutic agents that do cross the BBB are systemically administered.

Some devices and therapies have been developed to administer therapeutic agents to cerebrospinal fluid (CSF) to address some of these challenges. Such devices and therapies have typically been configured to deliver a bolus of therapeutic agent to a cerebral ventricle or to chronically administer the therapeutic agent to intrathecal space of the spinal canal. Such approaches have shortcomings for treatment of diseases of the brain. For example, such approaches lack the ability to achieve adequate spatially and temporally exposure of a therapeutic agent. Bolus administration of a therapeutic agent may not provide consistent therapeutically effective concentrations of the therapeutic agent, and intrathecal administration may not provide for sufficiently high concentrations of therapeutic agent in the brain due to, for example, gravitational forces and relatively limited CSF circulation.

Monitoring of a state of a disease, subject or therapy, such as concentrations of therapeutic agents in the brain, may also present challenges. For example, accurate estimates of concentrations of therapeutic agents in the brain may not always be readily achieved through routine blood or urine analysis. In addition, withdrawing CSF to obtain more accurate estimates of central therapeutic agent concentrations is invasive and may present risks.

For those therapies that include direct intracerebral ventricular delivery of therapeutic agents through, for example, an implantable infusion pump or port, CSF may be withdrawn through a catheter configured to deliver the therapeutic agent to the CSF from the pump or port. However, withdrawing CSF through the same lumen of a catheter that has been used to deliver therapeutic agent may not provide a clean sample of CSF. That is, the CSF may include therapeutic agent that was present in the lumen of the catheter and thus may not provide for accurate estimates of concentration of the therapeutic agent in the CSF. In addition, the CSF or the components of the CSF that maybe measured may interact with the material defining the lumen of the catheter, which may adversely affect subsequent delivery of the therapeutic agent. Furthermore, withdrawing CSF through the same lumen of the catheter that has been used to delivery therapeutic agent requires an interruption in the delivery of the therapeutic agent. The interruption of delivery can lead to cessation of therapy and other substantial consequences.

The use of separate catheters or separate lumens of a catheter for delivering therapeutic agents to the cerebral ventricles and for withdrawing CSF from the cerebral ventricles has been proposed. However, considerations for differences between infusion pathways and aspiration pathways have been lacking.

SUMMARY

The present application relates to, among other things, an implantable medical device comprising two or more separate fluid pathways. A first pathway is configured for withdrawing CSF from a CSF-containing space, and a second pathway is configured for infusing fluid, such as a therapeutic fluid, into a subject, such as into a CSF-containing space of the subject. A filter, such as filter configured to prevent flow of a microbe therethrough, may be positioned in the second pathway for infusing the fluid, and first pathway for withdrawing (e.g., aspirating or draining) the fluid may comprise no filter.

A microbial filter may become clogged over time due to passage of CSF through the filter. CSF proteins or cells that may be in the CSF may accumulate on a filer as CSF is aspirated through the filter, which accumulation of proteins and cells may eventually clog the filter. If a microbial filter were disposed across a passageway of an implantable device through which CSF is withdrawn, the passageway may eventually become unsuitable for passage of CSF due to the filter clogging, which may require invasive explant of the device to replace the filter or may reduce usability of the device. In addition, if a microbial infection is present in the CSF, the microbe responsible for the infection may be removed from the CSF if it were passed through a microbial filter. Thus, the presence of a microbial filter in the first fluid pathway for withdrawing CSF may prevent the ability to detect an infection in the withdrawn CSF.

Accordingly, the first pathway of the devices described herein that are configured for withdrawing CSF may comprise no filter or may comprise a filter having a sufficiently large pore size such that clogging or removal of microbes does not occur. Preferably, the first pathway does not comprise a filter. Advantageously, the fluid pathways for withdrawing CSF as described herein do not become clogged or are less likely to become clogged than fluid pathways comprising a microbial filter. Because the CSF-withdrawing first pathways of the devices described herein are less likely to clog, the device are less likely to be explanted and are more likely to continue to provide full functionality.

The device having a first pathway for withdrawing CSF from a CSF-containing space and a second pathway configured for infusing fluid into a subject, such as into the CSF-containing space of the subject, may be configured to be implanted in proximity to a skull. The device may be configured to be anchored to the skull through, for example, screws. The device may be configured to be at least partially received in a burr hole in the skull. The device may be configured to be implanted in proximity to a spine or may be configured to be implanted in any other suitable location of a patient.

The device may comprise, or may be configured to be connected to, a catheter comprising a first lumen and a second lumen or may comprise, or be configured to be connected to, a first catheter comprising a first lumen and a second catheter comprising a second lumen. The first lumen may be in fluid communication with the first fluid pathway of the device. The second lumen may be in fluid communication with the second fluid pathway of the device.

Preferably, the device and catheter or catheters, which may be associated with the device are configured to deliver fluid to a cerebral ventricle and to withdraw CSF from a cerebral ventricle. However, the device and catheter or catheters may be configured to deliver fluid to, or withdraw CSF from, any suitable CSF-containing space.

In some aspects described herein, an implantable medical device for withdrawing fluid from a CSF-containing space of a subject and from infusing fluid into the subject comprises a first inlet configured to be accessed by a needle for withdrawing CSF; a first outlet; a first fluid pathway extending from the first inlet to the first outlet; a second inlet; a second outlet; and a second fluid pathway extending from the second inlet to the second outlet. The device further includes one or more CSF catheters comprising a first lumen, a first distal opening in fluid communication with the first lumen, a second lumen and a second distal opening in fluid communication with the second lumen. The first lumen is in fluid communication with, or is configured to be placed in fluid communication with the first fluid pathway. The second lumen is in fluid communication with, or is configured to be placed in fluid communication with the second fluid pathway. The first distal opening is configured to be placed in the CSF-containing space of the subject. The first fluid pathway is free of a filter configured to prevent passage of a microbe.

The second fluid pathway may comprise a filter configured to allow passage of a therapeutic fluid and configured to prevent passage of a microbe. The second distal opening may be positioned in the CSF-containing space. Preferably, the first and second distal openings are configured to be positioned in a cerebral ventricle, such as a lateral ventricle.

Also provided herein are methods of implanting the implantable cranial medical devices and associated catheter or catheters, as well as methods of treating, monitoring, or treating and monitoring a disease of state of a subject using the implantable cranial medical devices.

The details of one or more aspects of the disclosure are set forth in the accompanying drawings and the description below. Other features, objects, and advantages of the techniques described in this disclosure will be apparent from the description and drawings, and from the claims.

While the invention is susceptible to various modifications and alternative forms, specific embodiments thereof are shown by way of example in the drawings and may herein be described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

Like numbers used in the figures refer to like components and steps. However, it will be understood that the use of a number to refer to a component in a given figure is not intended to limit the component in another figure labeled with the same number. In addition, the use of different numbers to refer to components in different figures is not intended to indicate that the different numbered components cannot be the same or similar to other numbered components.

DETAILED DESCRIPTION

The present disclosure relates to, among other things, implantable medical devices, such as devices for withdrawing (e.g., aspirating or draining) CSF from the CSF-containing space of a subject and delivering a fluid, such as a therapeutic fluid, to the subject. The fluid may be delivered to the CSF-containing space of the subject. The devices include a first fluid pathway for withdrawing CSF and a second fluid pathway for introducing the therapeutic fluid. The first fluid pathway is free of (does not include) a filter configured to prevent passage of a microbe.

CSF fluid may contain proteins, cells, or other components that may deposit and accumulate on a filter over time, which may eventually cause blockage if the filter has sufficiently small pore size to prevent passage of a microbe. Microbial filters may have a pore size 0.45 microns or less, such as 0.22 microns or less.

The ability to withdraw CSF through a microbial filter over time may diminish if a microbial filter is present in a passageway through which the CSF is withdrawn. Diminished ability to withdraw CSF through the first fluid pathway of the device may reduce usability of the device (e.g., only the delivery pathway may remain useable). In addition, if a microbial infection is present in the CSF, the microbe responsible for the infection may be removed from the CSF if it were passed through a microbial filter. Thus, the presence of a microbial filter in the first fluid pathway may prevent the ability to detect an infection in withdrawn CSF. For at least these reasons, the first fluid pathway of the devices described herein do not contain a filter configured to prevent passage of a microbe. In some embodiments, the first fluid pathway does not comprise a filter having a pore size of 0.45 microns or less. In some embodiments, the first fluid pathway does not comprise any filter.

The second fluid pathway may comprise a filter configured to allow passage of the therapeutic fluid and configured to prevent passage of a microbe. In some embodiments, the second fluid pathway of the device may be coupled to an infusion system that comprises a microbial filter in an infusion pathway in communication with the second pathway. In such embodiments, second fluid pathway of the device may be free of a microbial filter or may comprise a microbial filter.

If the second fluid pathway comprises a filter, the filter is preferably configured to prevent passage of a microbe therethrough. For example, the second fluid pathway may comprise a filter having a pore size of 0.45 microns or less. A filter having a pore size of 0.45 microns is a filter that prevents passage of particles having a diametric dimension of 0.45 microns or greater. The second fluid pathway may comprise a filter having a pore size of 0.22 microns or less or 0.2 microns or less.

The devices described herein comprise a first inlet, a first outlet, and a first fluid pathway that extends from the first inlet to the first outlet. The first inlet may be accessible by a needle. Preferably, the device is implanted such that the first inlet is accessible by the needle when the needle is inserted through the skin of the subject. For example, the device may be implanted such that the first inlet is implanted subcutaneously, and the needle may percutaneously access the first inlet. The first inlet may be configured to receive and engage the needle such that the needle may be used to aspirate CSF through the first fluid pathway.

The first outlet may be operatively coupled to or may be configured to be operatively coupled to a first lumen of a CSF catheter, such that the first lumen is in fluid communication with the first pathway. The CSF catheter comprises a first distal opening in fluid communication with the first lumen. The first distal opening of the CSF catheter is configured to be placed in the CSF-containing space. The CSF from the CSF-containing space may flow through the first distal opening into the first lumen, through the first passageway towards the first inlet and into the needle.

The devices described herein comprise a second inlet, a second outlet, and a second fluid pathway that extends from the second inlet to the second outlet. The second inlet may be accessible by a needle or may be operatively coupled to an accessory device catheter. The accessory device catheter may operatively couple an accessory device, such as an infusion device, to the second pathway. When the second inlet is configured to be accessible by a needle, the device is preferably implanted such that the second inlet is accessible by the needle when the needle is inserted through the skin of the subject. For example, the device may be implanted such that the second inlet is implanted subcutaneously, and the needle may percutaneously access the second inlet. The second inlet may be configured to receive and engage the needle such that the needle may be used to infuse a fluid through the second fluid pathway.

The second outlet may be operatively coupled to or may be configured to be operatively coupled to a CSF catheter having a second lumen and a second distal opening in fluid communication with the second lumen. When the second lumen is operatively coupled to the second outlet, the second lumen is in fluid communication with the second fluid pathway. The second distal opening may be placed in any suitable tissue of the subject. Preferably, the second distal opening is placed in the CSF-containing space. Fluid, such as a therapeutic fluid, may be introduced through the second inlet, flow through the second fluid pathway, through the second lumen, through the second opening of the CSF catheter and into the CSF-containing space.

The implantable medical device may comprise a housing. The housing may define an exterior surface of the port. The housing may be formed from one or more parts. As an example, different parts of the housing may be secured relative to one another by threaded engagement, snap fit engagement, interference fit engagement, may be welded, adhered, or otherwise bonded to one another, or the like, or combinations thereof. Preferably, different parts of the housing are connected to one another in a fluid tight manner. Preferably, different parts of the housing are welded together The housing of the device may comprise any suitable material. For example, the housing may be formed from one or more of a metallic material, a plastic material, a ceramic material, and a glass material. For example, the housing may comprise one or more of a high performance thermoplastic or relatively rigid plastic material, such as polyurethane, polycarbonate, polysulfone, polyether ether ketone (PEEK), nylon, and Ultra High Molecular Weight Polyethylene (UHMWPE); and a biocompatible metal, such as a stainless steel alloy, titanium, and nitinol. Preferably, the material is compatible with magnetic resonance imaging (MRI). Preferably, the housing comprises a biocompatible material or comprises an exterior biocompatible coating.

In some embodiments, device comprises a sleeve configured to cover one or more portions of the housing. The sleeve may be formed from one or more materials that are softer, more compliant, or softer and more compliant than the housing. The sleeve may be formed from any suitable material or materials. For example, the sleeve may comprise one or more of silicone and a thermoplastic elastomer. The sleeve is preferably biocompatible. The sleeve may be coated with or comprise a lubricious material, such as a hydrogel. The sleeve may serve to absorb impact that may occur to the patient's skin over the first port, which may reduce potential damage to the port or the patient. The sleeve may serve to reduce tissue erosion over time, particularly if the sleeve is formed from lubricious material or a material that is softer or more compliant than the housing. The sleeve may comprise one or more antimicrobial agent, such as antimicrobial silver and antibiotics. For example, the sleeve may be impregnated with one or antibiotics, such as minocycline and rifampin.

The first and second fluid pathways of the device may be configured in any suitable manner. Preferably, the first and second fluid pathways each extend within an interior of the housing. For example, the first fluid pathway may extend from a first inlet in the housing to a first outlet in the housing, and the second fluid pathway may extend from a second inlet in the housing to a second outlet in the housing.

The fluid flow paths may be formed in any suitable manner and form any suitable material or materials. The fluid flow paths, or portions thereof, may comprise passageways formed from one or more parts. In some examples, the passageway is formed from a lumen within tubing. In some examples, the passageway is formed from a channel in a solid part that is coupled to a second part to enclose the passageway. In some embodiments, the fluid pathways are formed by the housing. For example, the fluid pathways may be formed in a mold of the housing, micromachined in a component of the housing, may be formed by void spaced generated by assembling components of the housing, or the like. Preferably, the material lining the interior of the fluid pathway is compatible with fluid that flows through the pathway, such as a fluid containing a therapeutic agent or CSF. Preferably, the therapeutic agent or excipients or CSF do not sorb to or react with the material defining the fluid pathways. For purposes of the present disclosure, "sorb" refers to one or both of adsorb and absorb.

The structural material forming the fluid pathways may be compatible with the fluid or the structural material may be coated with a compatible material.

Any suitable material or materials may define the fluid pathways of the implantable cranial medical device. In some embodiments, the material defining the fluid pathways comprises one or more of metallic material, polymeric material, ceramic material, or glass material. For example, the material defining the fluid pathways may comprise one or more of a high performance thermoplastic or relatively rigid plastic material, such as polyurethane, polycarbonate, polysulfone, PEEK, nylon, and UHMWPE; and a biocompatible metal, such as a stainless steel alloy, titanium, and nitinol.

The device comprise a self-sealing septum disposed across the first inlet. The septum may allow a percutaneously inserted needle to enter the first inlet and may seal once the needle is withdrawn. The self-sealing septum may be made of any suitable material or materials. For example, the self-sealing septum may be formed from an elastomeric material. Preferably, the elastomeric material is white listed by the U.S. Food and Drug Administration (FDA) and is U.S. Pharmacopeia (USP) Class VI approved. The self-sealing septum may comprise silicone, a polyethylene, or the like, and combinations thereof.

The first inlet may be tapered or comprise one or more tapered components, such as a ferrule, to guide the needle into proper position and fit in the inlet. The tapered nature of the inlet may accommodate needles of a variety of sizes. For example, a ferrule or funnel-shaped inlet may accommodate needles with a range of sizes from about 16 gauge to about 25 gauge, such as from about 18 gauge to about 22 gauge. The gauge of needle employed may vary depending on the material introduced or withdrawn from the port. For example, a smaller gauge needle may be more desirable for more viscous fluids of fluids containing larger molecules or particles, such as cells or proteins.

Preferably, the first inlet is configured to receive non-coring needles, such as Huber needles or butterfly needles. Non-coring needles may be designed with a deflected or offset 'B' bevel point. Such a tip has the advantage of parting rather than cutting a plug from or coring the septum and may create a more comfortable injection. Using a non-coring needle, such as a Huber needle, may preserve the integrity of the septum and may prevent a plug of septum material from being cut and passed into the CSF.

The first inlet may comprise a seal, such as an O-ring or the like, to sealingly engage an outer surface of the needle when the needle is received in the inlet. Preferably, a sufficient seal is created to allow a relative negative pressure in the first passageway to cause CSF to flow into the needle received in the first inlet.

The second inlet may be configured to receive a needle for infusing fluid to the subject. A self-sealing septum may be disposed across the second inlet. The second inlet may be tapered or comprise one or more tapered components, such as a ferrule, to guide the needle into proper position and fit in the inlet. Preferably, the second inlet is configured to receive non-coring needles, such as Huber needles or butterfly needles. The second inlet may comprise a seal, such as an O-ring or the like, to sealingly engage an outer surface of the needle when the needle is received in the second inlet. Preferably, a sufficient seal is created to allow sufficient pressure in the second passageway to fluid to flow through the second pathway, the second lumen, and the second distal opening into the subject.

The device may comprise an accessory device catheter connector. The accessory device catheter connector may be configured to couple to a catheter configured to operatively couple the device to an accessory device, such as an infusion device. The accessory device catheter connector may define the second inlet.

A system may include the accessory device and the accessory device catheter. The accessory device catheter may be tunneled subcutaneously between the accessory device catheter connector and the accessory device. The accessory device may be an infusion device. The infusion device may be implantable or non-implantable. The non-implantable infusion device may be an ambulatory device or a stationary device. The infusion device may be manually powered, electromechanically powered, chemically powered, or otherwise powered. In some examples, the infusion device may comprise a piston pump, a peristaltic pump, an osmotic pump, a plunger, or the like. Examples of existing infusion devices that may be used include those manufactured by Medtronic, Inc. and Tricumed Medizintechnik GmbH.

The device may comprise one or more CSF catheter connectors. The one or more CSF catheter connectors may be configured to couple to a catheter configured to extend from the CSF catheter connector to a CSF-containing location of a subject. The one or more CSF catheter connectors preferably define the first and second outlets. Preferably, the CSF catheter connector is configured to couple to a CSF multi-lumen catheter having a first lumen and a second lumen. When connected to the CSF catheter connector, the first lumen is placed in fluid communication with the first fluid pathway, and the second lumen is placed in fluid communication with the second fluid pathway.

A catheter connector (e.g. accessory device catheter connector or CSF catheter connector) may be coupled to a catheter (e.g., accessory device catheter or CSF catheter) in any suitable manner. For example, the catheter and the catheter connector may comprise quick-release couplings, luer lock fittings, snap connect couplings, or the like. In some examples, the catheter is configured to be coupled to the catheter connector via interference fit. The catheter connector may comprise a fitting, which may comprise external barbs, configured to be inserted into a lumen of the catheter to retain the catheter relative to the catheter connector and to place the lumen of the catheter in fluid communication with an appropriate fluid pathway of the first port.

In some embodiments, a catheter connector comprises a first portion of a compression fitting and a second portion of the compression fitting is placed over the catheter. Connecting the first and second portion of the compression fitting may compress the catheter to secure the catheter to the catheter connector. For example, the compression fitting may cause the catheter to compress against external barbs. The second portion of the compression fitting may comprise a compression ferrule and a connection element to connect to the first portion of the fitting on the catheter connector.

In some embodiments, the one or more CSF catheters are coupled to the CSF catheter connector by a manufacturer. In some embodiments, the one or more CSF catheters are coupled to the CSF catheter connector prior to implanting the one or more CSF catheters. In some embodiments, the one or more CSF catheters are coupled to the CSF catheter connector after the one or more CSF catheters are implanted (i.e., after a distal portion of a CSF catheter is placed in the CSF-containing space). A CSF catheter may be permanently or reversibly coupled to the CSF catheter connector.

At least one lumen (the "first lumen") of at least CSF catheter may be placed in fluid communication with a subject's CSF such that CSF may be withdrawn from a CSF-containing space through the first pathway of the device. In some embodiments, first and second lumens of one or more CSF catheters are placed in fluid communication with a CSF-containing space of a subject such that fluid may be withdrawn from and introduced to the CSF-containing space. The CSF catheter or catheters are preferably configured such that fluid may be withdrawn from or delivered to the CSF-containing space through the first and second pathways of the first port, respectively, without interference or mixing of the fluids that are being withdrawn from or delivered to the CSF-containing space through the other of the first and second pathways. In some embodiments, the CSF catheter or catheters are configured such that the first lumen may be used to withdraw CSF-containing fluid and a second lumen may be used to deliver fluid to tissue other than a CSF-containing space, such as brain parenchyma. Preferably, the CSF catheter or catheters are configured such that the second lumen delivers fluid to the CSF-containing space.

Preferably, the one or more CSF catheters are configured such that the first lumen may be placed in fluid communication with a cerebral ventricle, such as a lateral ventricle. Preferably, the one or more CSF catheters are configured such that the second lumen may be placed in fluid communication with a cerebral ventricle, such as a lateral ventricle. Preferably, the CSF catheter is a dual lumen catheter in which the first and second lumens are configured to be placed in fluid communication with a cerebral ventricle, such as a lateral ventricle.

A CSF catheter may have any suitable length to extend from a location in which the CSF catheter connector is implanted to a CSF-containing location of the subject. For example, if the CSF catheter connector of the device is implanted in proximity to a skull of the subject and the CSF catheter is configured to extend to a lateral cerebral ventricle, the CSF catheter may have a length from about 55 millimeters to about 80 millimeters, such as from about 60 millimeters to about 70 millimeters, or from about 62 millimeters to about 68 millimeters.

The CSF catheter may have any suitable outer diameter. Preferably, the outer diameter is from about 2 mm to about 4 mm, such as from about 2 mm to about 3 mm, or from about 2 mm to about 2.5 mm.

Preferably, the CSF catheter comprises two lumens. The two lumens may be oriented in any suitable manner. For example, the two lumens may be concentric, such as a lumen within a lumen (or catheter within a catheter) or may be side-by-side. Preferably, the outer surface of the brain catheter has a substantially circular cross-sectional shape.

The CSF catheter may comprise an inner wall running along the length of the catheter. The inner wall may separate the two lumens of the CSF catheter. The CSF catheter may comprise two semicircular (or D-shaped) cross-sectional shaped lumens running along the length of the catheter. The semicircular lumens may be of any suitable size. For example, the inner dimension of the semicircular lumens at their largest width may be in a range from about 0.9 millimeters to about 1.5 millimeters, such as from about 1.1 millimeters to about 1.5 millimeters, or from about 1.2 millimeters to about 1.4 millimeters. The inner dimension of the semicircular lumens at their smallest width may be in a range from about 0.4 millimeters to about 0.7 millimeters, such as from about 0.5 millimeters to about 0.6 millimeters, or from about 0.55 millimeters to about 0.6 millimeters. The inner dimensions of the first and second lumens may be the same or different. Preferably, the inner diameter of the first and second lumen are the same or substantially the same (e.g., do not vary by more than 10%).

The CSF catheter may comprise any suitable material. The material is preferably biocompatible and compatible with a therapeutic fluid that may be delivered through a lumen of the catheter. The material is preferably biocompatible and compatible with CSF that may be flow through a lumen of the catheter. Preferably, the material is biodurable. A biodurable material is a material that is compositionally and structurally stable for extended periods of time in a biological environment. Products made from such materials should not exhibit substantial breakdown, degradation, erosion, or deterioration of mechanical properties relevant to their employment when exposed to biological environments for periods of time commensurate with the use of the implantable device. An intended biological environment can be understood to be in vivo, i.e., associated with an implantable device in a patient. The period of implantation of a CSF catheter described herein may be weeks, months, or years. For example, a CSF catheter may be made from materials that are biodurable for at least 29 days, such as at least one year, at least three years, or at least five years.

Any suitable homopolymer, copolymer, blends of polymers or combinations of polymers may be used to form the CSF catheter. Preferably, the polymers used to make the catheters are flexible during both fabrication and assembly. Preferably, the CSF catheters are formed from materials that result in a flexible and soft catheter during its in vivo implantation period.

Preferably, the chemical composition and molecular structure is selected so that the catheter materials are flexible and soft but still remain biodurable and resist substantial breakdown, degradation, erosion, or deterioration of mechanical properties when exposed to therapeutic agents or excipients delivered over extended periods of time. Flexibility and softness are characteristics that tend to cause a catheter to lack biodurability and long-term compatibility in oxidative, hydrolytic, and body fluid contact environments. Accordingly, the choice of polymers should be carefully selected to achieve sufficient compatibility with the therapeutic agent and excipients, biodurability, flexibility, and softness.

Depending on compatibility with the therapeutic agent and excipients to be employed, the CSF catheter may comprise cross-linked silicone, which may form flexible catheters. The glass transition temperature (Tg) of cross-linked silicone may depend on the cross-link density. In some embodiments, the brain catheter may comprise cross-linked silicone having a Tg below −40° C., such as below −90° C. In some instances, components of therapeutic fluids may interact with a cross-linked silicone catheter. In some instances, components of therapeutic fluids may leach or extract components or parts of a cross-linked silicone catheter. Swelling and leaching or extraction may affect the biodurable nature of soft and flexible cross-linked silicone and its capability to maintain dimensions or wall thickness and structure to provide multiple stable fluid paths over extended periods of time.

In some embodiments, a CSF catheter comprises polyurethane. Preferably, the CSF catheter comprising polyurethane resists degradation in oxidative, hydrolytic, and body fluid contact environments. The polyurethane may comprise biostable hard and soft segments. The polyurethane may comprise a higher hard segment content. Such polyurethanes may resist degradation in oxidative, hydrolytic, and enzymatic changes under physiological conditions and body fluid contact. In some embodiments, the CSF catheter comprises a polyurethane containing hard and soft segments that are formed by reacting a diol or polyol (an alcohol with more than two reactive hydroxyl groups per molecule) with a diisocyanate or a polymeric isocyanate in the presence of suitable catalysts and additives. The isocyanates (sometime chain extended with diols) form the hard segments and the polyols form the soft segments, with the segments linked by the urethane bonds formed from the reaction between the polyols and diisocyanate.

In some embodiments, the hard segment of the polyurethane comprises of an aromatic isocyanate. In some embodiment, the hard segment of the polyurethane comprises an aliphatic isocyanate. Preferably, the hard segment comprises an aromatic isocyanate as.

In some embodiments, the soft segment of the polyurethane comprises of a polyether. In some embodiments, the soft segment of the polyurethane comprises of a polycarbonate. The soft segment may provide suitable flexibility for use in single lumen catheters and multi-lumen catheters.

In some embodiments, a CSF catheter comprises a polyurethane that is semi-crystalline with higher hardness. The semi-crystalline nature of the polyurethane polymers makes them resistant to swelling and leaching when in contact with CSF, therapeutic fluids, and therapeutic fluids having high concentration therapeutic agents. Semi-crystalline polyurethanes may be resistant to degradation in oxidative, hydrolytic, and enzymatic changes and body fluid contact environments. Higher hardness may provide a polyurethane resistant to swelling and leaching when in contact with CSF, therapeutic agents, and highly concentrated therapeutic agents. Higher hardness polyurethanes may be resistant to degradation in oxidative, hydrolytic, and enzymatic changes and body fluid contact environments. A polyurethane with a higher hardness (i.e., higher A or preferably D hardness scale) may have less soft segment and higher crystallinity, which may slow diffusion and interaction with solvents and solutions. Accordingly, CSF catheters comprising polyurethane may be less susceptible to swelling or attack by solvents and solutions of therapeutic fluids.

A CSF catheter comprising a polyurethane with higher hardness may allow for reduced wall thickness and may provide for processing advantages for single lumen brain catheters and multi-lumen brain catheters.

In some embodiments, the catheter may be formed from a material having a Shore A hardness in a range from about 70 A to about 110 A. In some embodiments, the catheter may be formed from a material having a Shore A hardness above 80 A or preferably above 90 A. In some embodiments, the catheter is formed from a material having a Shore D hardness of about 30D to about 70D, such as from about 40D to about 60D, or from about 50D to about 60D.

The CSF catheter may comprise a semicrystalline polymer other than a polyurethane. The semicrystalline polymers may be selected to provide resistance to degradation in oxidative, hydrolytic, and enzymatic changes and body fluid contact environments while maintaining the desired flexibility through thinner wall or lower wall thickness. In some embodiments, a CSF catheter comprises one or more of polyolefin, polyethylene, a fluorinated polymer, a fluorinated homopolymer, a fluorinated copolymer, a homopolymer of polyvinylidene difluoride (PVDF), a copolymer of PVDF, a copolymer of tetrafluoroethylene (TFE) and hexafluoro propylene (HFP), and polychlorotrifluoroethylene. A polyolefin may provide resistance to change during its in vivo life through its high crystallinity and long hydrocarbon chains, and a fluorinated polymer may provide resistance to change during its in vivo life through its high crystallinity and the inert nature of fluorine.

Some examples, of polymers that may be used to form a CSF catheter as described herein include aliphatic or aromatic, polycarbonate-based thermoplastic polyurethane, such as CARBOTHANE (available from Lubrizol, Wickliffe, Ohio, USA), perfluoroelastomers, such as KALREZ (available from DuPont, Wilmington, Delaware, USA); PVDF, such as KYNAR FLEX (available from Daikin, Osaka, Japan) or KYNAR ULTRAFLEX (available from Arkema, Colombes, France); fluorinated ethylene propylenes, such as NEOFLON (available from Daikin, Osaka, Japan).

It should be understood that identifying a polymer or polymers that provide resistance to substantial breakdown, degradation, erosion, or deterioration of mechanical properties but at the same time is flexible while maintaining catheter dimensions, wall thickness, and structure is not trivial, in particular if the catheter is intended for implanted use over extended periods of time. In addition, it should be understood that the design challenges associated in identifying a suitable polymer or polymers for forming the catheters in combination with design concerns associated with the first port described herein, some of which are described above, present substantial challenges. Accordingly, the design of a suitable first port as described herein with a suitable CSF catheter was not a trivial task.

In some embodiments multiple single lumen CSF catheters are made from the same polymer or polymers. In other embodiments, the multiple single lumen CSF catheters are made from different polymers. In some embodiments, multiple single lumen CSF catheters are separated from each other. In other embodiments, the two single lumen CSF catheters are bonded to each other, such as via chemical bonding or thermal bonding. In some embodiments, more than one lumen of a multi-lumen CSF catheter is made from the same polymer or polymers. In other embodiments, lumens of a multi-lumen lumen CSF catheter are made from different polymers. In some embodiment, all lumens of a multi-lumen CSF catheter are made from the same polymer or polymers. In other embodiments, two or more lumens of a multi-lumen CSF catheter are made from two or more different polymers.

Exterior surfaces of the CSF catheter preferably comprise a material or materials that are biocompatible. Preferably, exterior surfaces of the CSF catheter inhibit tissue adhesion. Preferably, exterior surfaces of the CSF catheter are easily inserted. A hydrophilic coating, such as a hydrogel, may be applied to an exterior surface to cause the exterior surface to be lubricious to facilitate insertion of the catheter during implantation. The exterior surface of the catheter may be coated with polytetrafluoroethylene (PTFE) or another polymer to improve insertability, decrease adhesion, or increase insertability and decrease adhesion. In some embodiments, the structural material of the catheter is sufficiently insertable and sufficiently resists tissue adhesion without an additional coating. If a coating is applied, the surface of the catheter preferably includes functional groups that may covalently bind with a coating. The surface of the catheter may be treated to introduce functional groups, or the functional groups may be present in the material forming the catheter.

The CSF catheter may include or may be coated with an antimicrobial material, such as antimicrobial silver or an antibiotic. In some embodiments the CSF catheter includes or is coated with a composition comprising a combination of minocycline and rifampin. In some embodiments, the CSF catheter is soaked in a solution comprising an antimicrobial agent, and the antimicrobial agent is taken up by the material forming the CSF catheter.

The CSF catheter may comprise radiopaque material visible by imaging, such as X-ray or magnetic resonance imaging (MM). The CSF catheter may comprise radiopaque material throughout the catheter, may comprise a concentrated area of radiopaque material, or may comprise radiopaque material throughout the catheter and may comprise a concentrated area of radiopaque material. The CSF catheter may comprise a concentrated radiopaque material at a distal end portion. The CSF catheter may comprise one or more concentrated radiopaque bands or markings along the length of the marker that may be used to determine the depth of the catheter during or after implantation.

The CSF catheter may comprise any suitable radiopaque material. Examples of suitable radiopaque material includes barium sulfate, tantalum, and titanium.

In some embodiments, barium sulfate is blended with a polymer forming the catheter such that the barium sulfate is distributed through the catheter. Any suitable concentration of barium sulfate may be used. In some examples, about 5% barium sulfate by weight to about 20% barium sulfate by weight is blended into the polymer forming the catheter. For example, about 10% barium sulfate by weight to about 15% barium sulfate by weight, or about 12% barium sulfate may be blended into the polymer forming the catheter. 12% barium sulfate blended into the polymer was empirically determined to provide a suitable balance of a number of factors, including (i) ability to visualize the catheter throughout the implant process as it penetrates, (ii) manufacturability of thin-walled dual lumen catheter, and (iii) compatibility with fluids comprising high concentration therapeutic agents that may be infused through the catheter. Balancing these factors may achieve biocompatibility and biostability for the life of its implant, such as 5 years or more. In some embodiments, a tantalum marker, such as a tantalum bead, is positioned in the CSF catheter at the distal end portion.

The CSF catheter may comprise one or more openings in communication with a lumen of the catheter through which fluid may flow. The CSF catheter may comprise any suitable number of openings in communication with each lumen. For example, the CSF catheter may comprise one to ten or more openings in communication with each lumen, such as two to six openings or three to four openings in communication with each lumen. The CSF catheter may have the same number of openings in communication with the first lumen as in communication with the second lumen. The CSF catheter may have a different number of openings in communication with the first lumen than in communication with the second lumen.

The openings may be of any suitable size and may be configured in any suitable manner. The openings have a diameter or width of from about 0.2 millimeters to about 1 millimeter, such as from about 0.4 millimeters to about 0.6 millimeters, or about 0.5 millimeters. The openings may have the same or different diameters or widths.

The openings may be any suitable shape. For example, the openings may have circular or elliptical cross-sectional shapes, rectangular cross-sectional shape, triangular cross-sectional shape, or the like, or combinations thereof.

The openings may always be open or may be configured to open due to a pressure differential in the lumen of the catheter and CSF in which the distal portion of the brain catheter is implanted. For example, the openings may comprise slits that open due to relative positive pressure in the lumen when fluid is infused through the lumen to the CSF or due to relative negative pressure in the lumen when CSF is aspirated through the lumen. The slit may be cut into a resilient material that flexes when under pressure but returns to an original shape as pressure equalizes.

The openings may be positioned at any suitable location of the catheter. In some embodiments, the one or more openings of the CSF catheter in communication with a lumen configured to infuse therapeutic fluid (e.g., the lumen in communication with the second fluid pathway of the first port) may be positioned a short distance from the distal tip of the CSF catheter. The one or more openings of the CSF catheter in communication with a lumen through which CSF is configured to be aspirated (e.g., the lumen in communication with the first fluid pathway of the first port) may be positioned at or in proximity to the distal tip. Distancing infusion openings from aspiration openings may allow for infused fluid to mix with CSF so that aspirated CSF better represents concentrations of therapeutic agent in CSF than if the infusion and aspiration openings were in proximity to each other. If the infusion and aspiration openings are located adjacent to one another, then aspirated CSF may have higher concentration that CSF at a location more remote from the aspiration lumen. If the aspiration and infusion openings are located further apart from one another, then the aspirated fluid would be more representative of the entire CSF.

In addition to positioning aspiration and infusion openings longitudinally apart (closer to or further from the distal tip), the aspiration openings and the infusion openings may be placed on generally opposing sides of the CSF catheter. For example, the aspiration openings and the infusion openings may be positioned from about 160 degrees to about 180 degrees radially apart from one another. By positioning the infusion and aspiration lumens radially apart, substantial mixing of CSF with therapeutic fluid infused through an infusion opening may occur prior to aspirating the CSF through an aspiration opening.

In addition to positioning aspiration and infusion openings away from each other in a staggered manner in the cerebral ventricle, the position of the openings may be substantially separated such that the infusion holes are placed within a tissue location in the central nervous system, such as in the brain, other than a CSF-containing location, such as the cerebral ventricle, but the aspiration openings remain in the CSF-containing space.

The lumens of the CSF catheter may have the same or different lengths. The lumens of the CSF catheter may have a length that extends from a proximal end portion, which may be coupled to the CSF catheter connector of the first port, to the distal-most opening in the catheter in communication with the respective lumen. If the lumens of the CSF catheter are configured to carry fluid to or from the same CSF-containing location, such as a cerebral ventricle, the lumens may have the same or substantially similar lengths. If the lumens of the CSF catheter are configured to carry fluid to or from different locations, such as a cerebral ventricle and brain parenchyma, the lumens may be of substantially different lengths. For purposes of the present disclosure, lumens having "substantially different" lengths are lumens that have lengths that differ by more than 10 percent. Lumens that have "substantially similar" lengths are lumens that have lengths that differ by 10 percent or less.

In some embodiments, the CSF catheter comprises multiple infusion openings positioned a distance from the distal tip, such as from about 3 millimeters from the distal tip to about 15 millimeters from the distal dip. For example, all the infusion openings may be positioned from about 3 millimeters to about 10 millimeters from the distal dip, or from about 4 millimeters to about 8 millimeters from the distal tip. In some embodiments, at least one aspiration lumen is positioned at the distal tip of the CSF catheter.

The implantable medical devices and systems described herein may be included in a kit. The kit may include a CSF catheter. The CSF catheter may be coupled to the implantable medical device in the kit or may be coupled by an end user, such as a healthcare professional. Preferably, the CSF catheter is coupled to the implantable medical device prior to packing in the kit. The kit may include a compression fitting to aid in connecting an accessory device catheter to an accessory device catheter connector of the implantable medical device. The kit may include fasteners, such as screws, configured to secure the implantable medical device to suitable tissue of the subject, such as the skull of the subject. The kit may include a tool, such as a screwdriver, to aid with deploying, holding, positioning, etc. the fasteners, such as screws. The kit may include a needle configured to access an inlet of the implantable medical device, which may be used for, for example, aspiration of CSF. The needle may be a non-coring needle, such as a Huber needle or a butterfly needle.

While only a few kit components are listed above, it will be understood that any component discussed herein may be included in a kit comprising an implantable cranial medical device.

The implantable medical devices and associated devices described herein may be implanted in any suitable manner. In some embodiments, a CSF catheter having a distal end and a proximal end is implanted such that the distal end is positioned in a CFS-containing region, such as an intrathecal space, a cisterna magna, or a cerebral ventricle, of a subject. Preferably, the CSF catheter is a dual lumen catheter comprising the first lumen and the second lumen. The proximal end of the CSF catheter may be coupled to the implantable device to place the first lumen of the dual lumen CSF catheter in communication with the first fluid path of the implantable medical device and the second lumen of the CSF catheter in communication with the second fluid path of the implantable medical device.

The CSF catheter may be coupled to the implantable medical device before or after the distal end of the CSF catheter is positioned in the CSF-containing space. Preferably, the CSF catheter is coupled to the implantable medical device prior to the CSF catheter being implanted. A stylet may be inserted through a fluid flow path, such as the first fluid flow path, of the implantable medical device and into a lumen, such as the first lumen, of the CSF catheter to facilitate implanting the CSF catheter into the CSF-containing space of a subject. For example, the stylet may be inserted through a septum of a port in communication with the first fluid path, through the first fluid path, and into the first lumen.

A subject, in which the implantable medical device and associated components may be implanted, may undergo a preoperative scan for surgical planning. A surgical navigation system may be employed during an implant procedure to facilitate placement of the CSF catheter. The CSF catheter may be radiopaque, may include one or more radiopaque markers, or may be radiopaque and include one or more radiopaque markers to allow visualization with the surgical navigation system employed. For example, Medtronic, Inc.'s AxiEM™ electromagnetic technology and StealthStation® Navigation System and B. Braun Aesculap division's Intraventricular Disposable Introducer Set™ may be used to facilitate implantation of the CSF catheter. Preferably, the distal end portion of the catheter is positioned in a cerebral ventricle of the subject. Preferably, the distal end portion of the catheter is positioned in a lateral ventricle. However, the distal end portion of the brain catheter may be placed in any suitable location, such as the cisterna magna or an intrathecal space.

Figure 1:
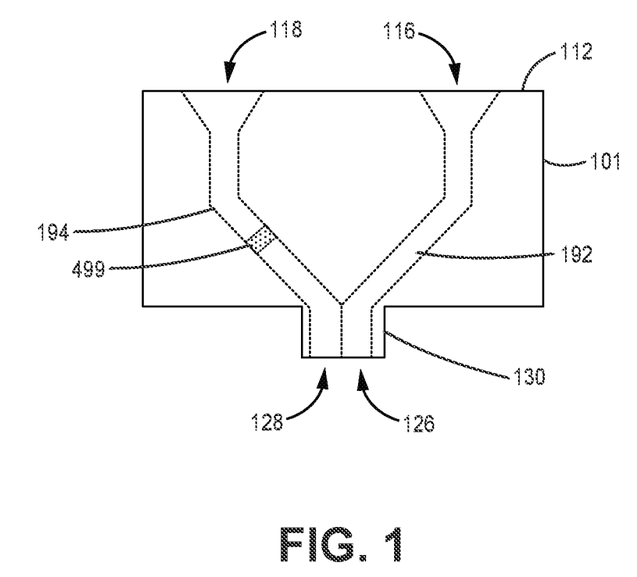
FIGS. 1 and 2 are schematic sectional views illustrating some components of embodiments of implantable medical devices with fluid flow pathways shown in dashed lines.
Figure 2:
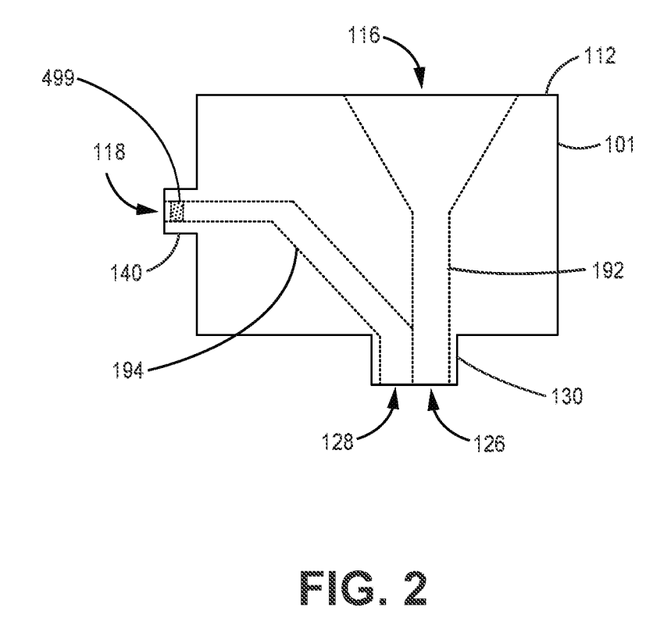
Figure 3:
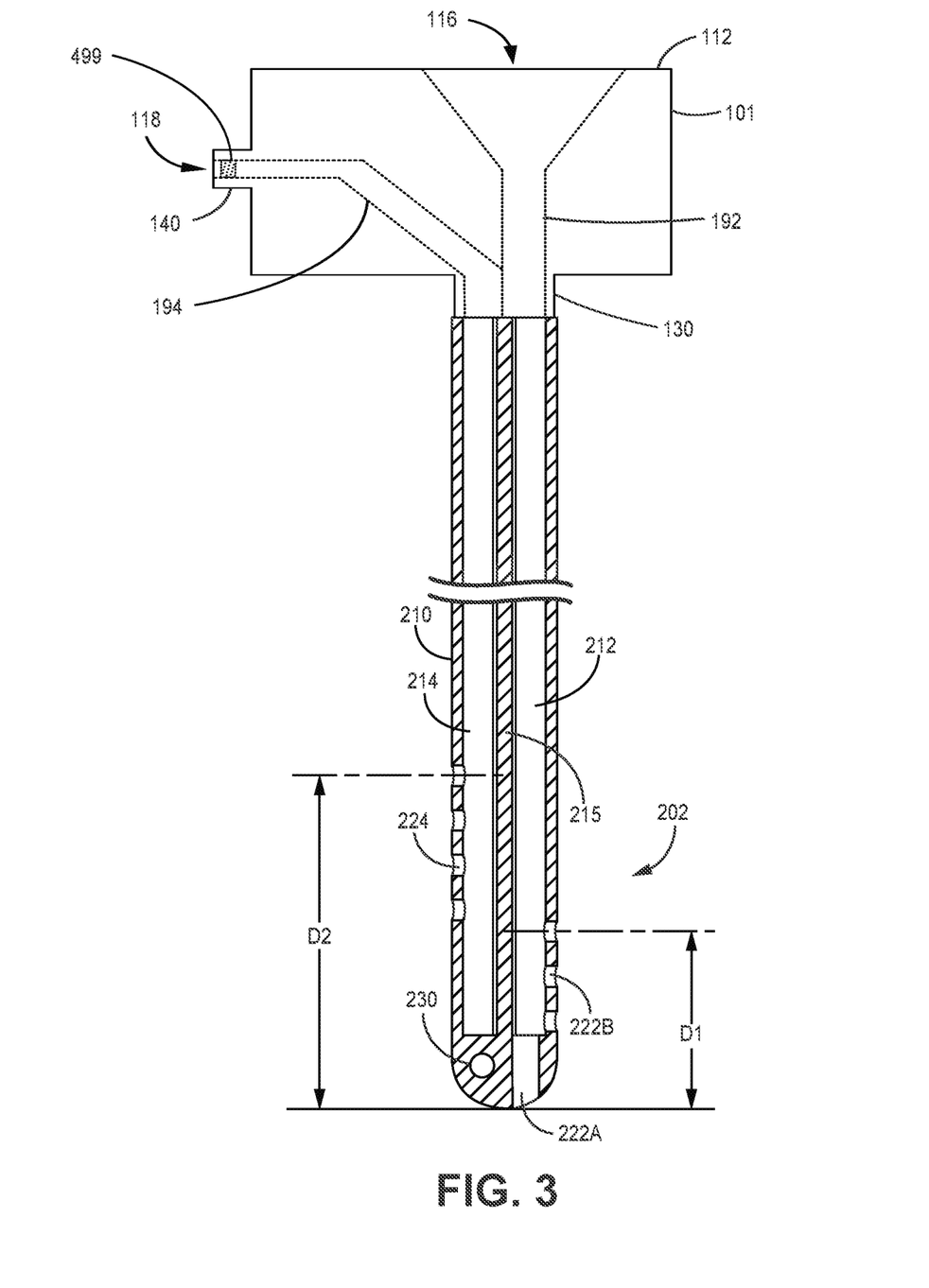
FIG. 3 is a schematic sectional view of the device of FIG. 2 and a CSF catheter.
Figure 4:
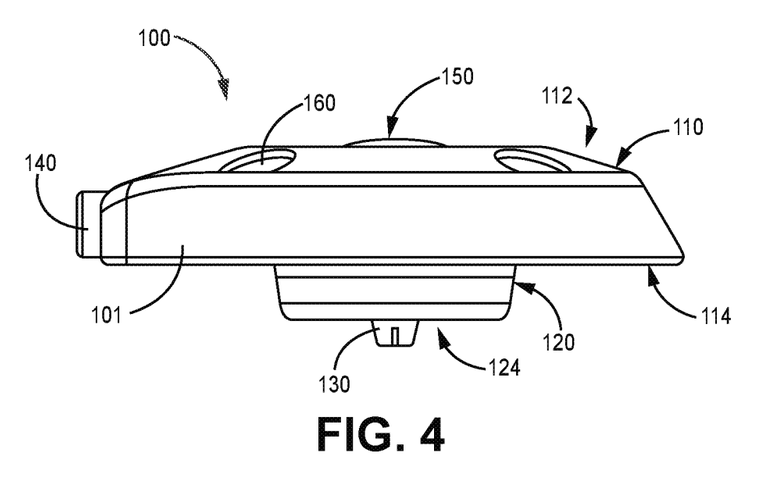
FIG. 4 is a schematic side view of an embodiment of an implantable cranial medical device.
Figure 5:
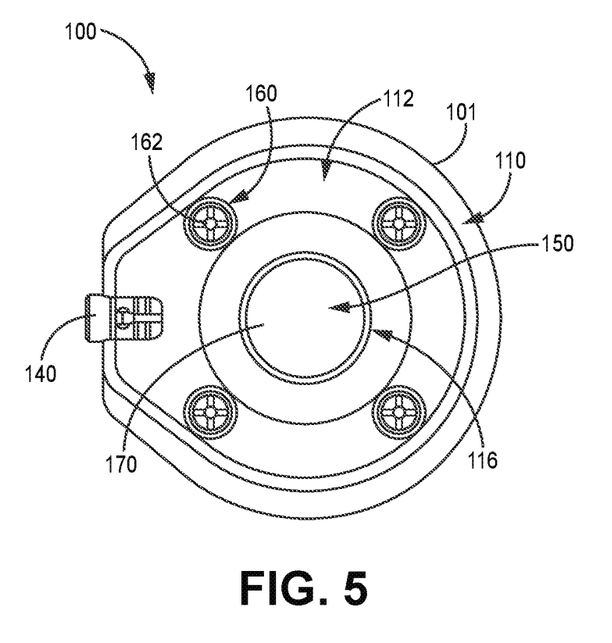
FIG. 5 is a schematic top view of an embodiment of the implantable cranial medical device depicted in FIG. 4.
Figure 6:
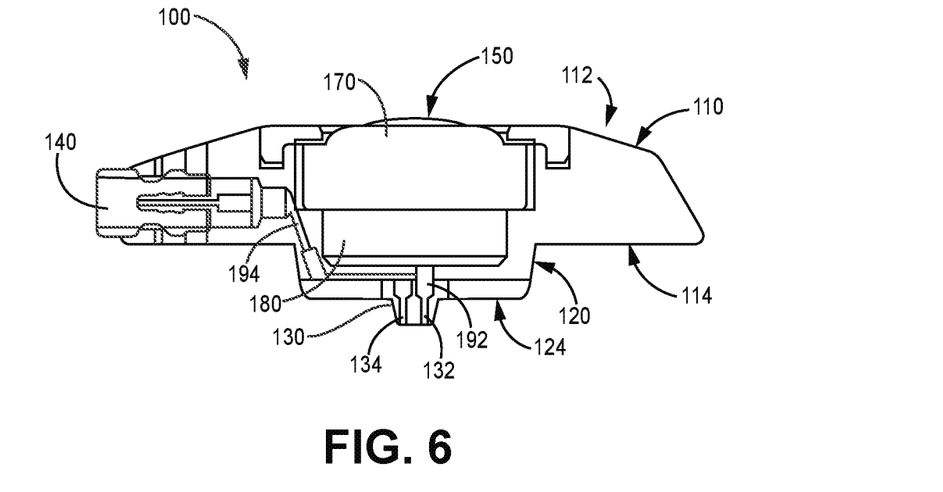
FIG. 6 is a schematic side view of the implantable cranial medical device depicted in FIG. 4 in which the housing is sectioned.

Referring now to FIGS. 1-3, an implantable medical device 100 comprises a first fluid pathway 192 extending from a first inlet 116 to a first outlet 126. The device 100 comprises a second fluid pathway 194 extending from a second inlet 118 to a second outlet 128. The first fluid pathway 192 is free of a filter. The second fluid pathway 194 comprises a filter 499. The filter 499 is positioned such that fluid that flows through the second fluid pathway 194 flows through the filter 499. The filter 499 may be positioned at any suitable location within the second fluid passageway 194.

The device 100 comprises a housing 101, which may define all or a portion of the exterior surface of the device 100.

The device 100 may comprise a CSF catheter connector 130 configured to operatively couple a CSF catheter to the device 100. The housing 101 may form the catheter connector 130 or one or more other components operatively coupled to the housing 101 may form the CSF catheter connector 130. The CSF catheter connector 130 may be configured to connect a CSF catheter having a first and second lumen or may be configured to connect to a first CSF catheter having a first lumen and to connect to a second CSF catheter having a second lumen. When the CSF catheter or catheters are operatively connected to the CSF catheter connector 130, the first lumen of the CSF catheter or catheters is in fluid communication with the first outlet 126 and the second lumen of the CSF catheter or catheters is in fluid communication with the second outlet 128.

In the embodiments depicted in FIG. 1, the first 116 and second 118 inlets are positioned at a top surface 112 of the device 100. The inlets 116, 118 are configured to receive a needle. Preferably, the first and second inlets 116, 118 are configured to receive different needles. The first inlet 116 may be configured to receive a first needle, and the second inlet 118 may be configured to receive a second needle. The first inlet 116 may be configured such that it cannot receive the second needle. The second inlet 118 may be configured such that it cannot receive the first needle. The needles and the inlets 116, 118 may be of certain sizes and shapes to permit the first needle to be inserted into the first inlet 116 but not the second inlet 118 and to permit the second needle to be inserted into the second inlet 118 but not the first inlet 116. In this manner, accidental infusion of therapeutic fluid into the second (CSF withdrawal) pathway 192 and accidental withdrawal of CSF through the first (infusion) pathway 194 may be avoided.

The first 116 and second 118 inlets are tapered to guide an appropriate needle into proper position and fit. The inlets 116, 118 and/or passageways 192, 194 may comprise seals (not shown), such as O-rings or the like, to sealingly engage an outer surface of a needle. The seals may prevent infused fluid introduced through a needle into the second passageway 194 from coming out through the second inlet 118 and may create a sufficient seal to create a relative negative pressure in the first passageway 192 to cause CSF to flow into a needle received in the first inlet 116.

The device 100 may comprise a first self-sealing septum (not shown) positioned across the first inlet 116. The device 100 may comprise a second self-sealing septum (not shown) positioned across the second inlet 118.

In the embodiment depicted in FIG. 2, the device 100 includes an accessory device catheter connector 140. The accessory device catheter connector 140 is configured to operatively couple an accessory device catheter to the device 100. The housing 101 may form the accessory device catheter connector 140 or one or more other components operatively coupled to the housing 101 may form the accessory device catheter connector 140. The accessory device catheter connector 140 may be configured to connect an accessory device catheter having a lumen. When the accessory device catheter is operatively connected to the catheter connector 140, the lumen of the accessory device catheter is in fluid communication with the second inlet 118 and second pathway 194 of the device 100. The accessory device may be an infusion device, a modified Ommaya or Rickman reservoir, or the like.

In FIG. 2, the filter 499 is depicted as being in the second pathway 194 in proximity to the accessory device catheter port 140. However, the filter 499 may be positioned at any suitable location in the second pathway 194.

FIG. 3 shows the device of FIG. 2 and a CSF catheter 200. The CSF catheter 200 is connected to the CSF catheter connector 130. The CSF catheter 200 includes a first lumen 212 and a second lumen 214 separated by a central wall 215 of the body 210 of the CSF catheter 200. The first lumen 212 is in fluid communication with the first fluid pathway 192, and the second lumen 214 is in fluid communication with the second fluid pathway 194.

The first lumen 212 is in communication with one or more openings 222 at the distal end portion 202. In the depicted embodiment, the first lumen 212 is in communication with three side openings 222B at the distal end portion 202 and a distal end opening 222A. The second lumen 214 is in communication with one or more side openings 224 at the distal end portion 202. In the depicted embodiment, the second lumen 212 is in communication with four side openings 224 at the distal end portion 202. The side openings 222A and 224 are positioned on generally opposing sides of the CSF catheter. The distance (D1) from the distal tip to the side opening 222A furthest from the distal tip is less than the distance (D2) from the distal tip to the side opening 224 furthest from the distal tip. Preferably, all the openings 224 in communication with the second lumen 214 are positioned away from the distal tip a distance greater than D1. The position and orientation of the openings 222A, 222B, 224 allow for therapeutic fluid that may be infused through the second lumen through side openings 224 to substantially mix with CSF prior to being aspirated through openings 222A, 222B and through the first lumen 215.

If D2 is substantially greater than D1, the CSF catheter may be suitable for withdrawing fluid from a cerebral ventricle through openings 222A and 222B and may be suitable for delivering fluid to brain parenchyma through openings 224. If D2 is not substantially greater than D1, the CSF catheter may be suitable for withdrawing fluid from a cerebral ventricle through openings 222A and 222B and delivering fluid to the CSF through openings 224.

The CSF catheter 200 depicted in FIG. 3, includes a radiopaque marker 230 visible by X-ray, magnetic resonance imaging (MM), or X-ray and MRI imaging so that the location of the distal end portion 202 may be readily determined. For example, the radiopaque marker 230 may comprise tantalum and may be embedded in the distal end portion 202 of the catheter 200 near the distal tip. The body 210 of the CSF catheter 200 may comprise barium sulfate or another radiopaque material (not shown) dispersed throughout. In some embodiments (not shown), the CSF catheter may include radiopaque markers at locations along the length of the CSF catheter to form depth markings that may be used to determine the depth of the catheter during or after implantation.

The devices shown in FIGS. 1-3 illustrate some example fluid flow pathways and filter locations that may be employed in a device as described herein. In the remaining figures, a more detailed description of embodiments of the device where the device is, or comprises, an implantable cranial device is shown. More information regarding such embodiments is provided in U.S. Patent Application No. 63/052,284, filed on Jul. 15, 2020, entitled IMPLANTABLE CRANIAL MEDICAL DEVICE, naming Cerebral Therapeutics, Inc. as Applicant and in U.S. Patent Application No. 63/209,835, filed on Jun. 11, 2021, entitled IMPLANTABLE CRANIAL MEDICAL DEVICE, naming Cerebral Therapeutics, Inc. as Applicant, which applications are hereby incorporated herein by reference in their entireties to the extent that they do not conflict with the disclosure presented herein.

Reference is now made to FIGS. 4-7 in which an embodiment of an implantable medical device 100 is shown. The embodiment of an implantable medical device 100 shown in FIGS. 4-7 includes an upper flange portion 110 having a top surface 112 and a bottom surface 114 and includes a lower portion 120 having a bottom major surface 124. Fastener feedthroughs 160 extend through the upper flange portion 110 from the top surface 112 to the bottom surface 114 and are configured to receive fasteners 162, such as screws, which may be used to anchor the housing to the skull of a subject in which the device 100 is implanted.

The device 100 includes a port 150 in communication with the first fluid path 192. The lateral edge of the port 150 is defined by the first inlet 116 defined by the top surface 112 of the upper flange portion 110. A self-sealing septum 170 extends across the inlet 116. When the device 100 is implanted, the port 150 is positioned and oriented to receive a needle inserted through the scalp such that a lumen of the needle is placed in fluid communication with the first fluid path 192.

The device 100 includes a reservoir 180 in communication with and forming a part of the first fluid path 192. The reservoir 180 is positioned such that insertion of a needle into the port 150 places a lumen of the needle in fluid communication with the reservoir 180. The reservoir 180 is disposed with the housing 101.

The device also includes an accessory device catheter connector 140 that extends substantially parallel with the bottom surface 114 of the upper flange portion 110 of the device 100. The accessory device catheter connector 140 is operably coupled to an opening defined by the upper flange portion 110 (such as second opening 118 depicted in FIG. 1). The accessory device catheter connector 140 defines a passageway in communication with the second fluid path 194 of the device 100. The accessory device catheter connector 140 is configured to operably couple to an accessory device catheter to place a lumen of the accessory device catheter in fluid communication with the second fluid path 194. The accessory device catheter may further be coupled to a device other than the implantable cranial medical device 100, such as an infusion device. The infusion device may implantable or non-implantable.

The implantable medical device 100 also includes a CSF catheter connector 130 having a first lumen 132 and a second lumen 134. The first lumen 132 may form the first outlet. The second lumen 134 may form the second outlet. The CSF catheter connector 130 extends from the bottom major surface 124 of the lower portion of the housing 120. The first lumen 132 of the CSF catheter connector 130 is operably coupled to the first fluid path 192. The second lumen 134 of the CSF catheter connector 130 is operably coupled to the second fluid path 194. The CSF catheter connector 130 is configured to operably couple to a dual lumen catheter, which may have a distal end. The distal end may be implantable in a cerebral ventricle.

Figure 7:
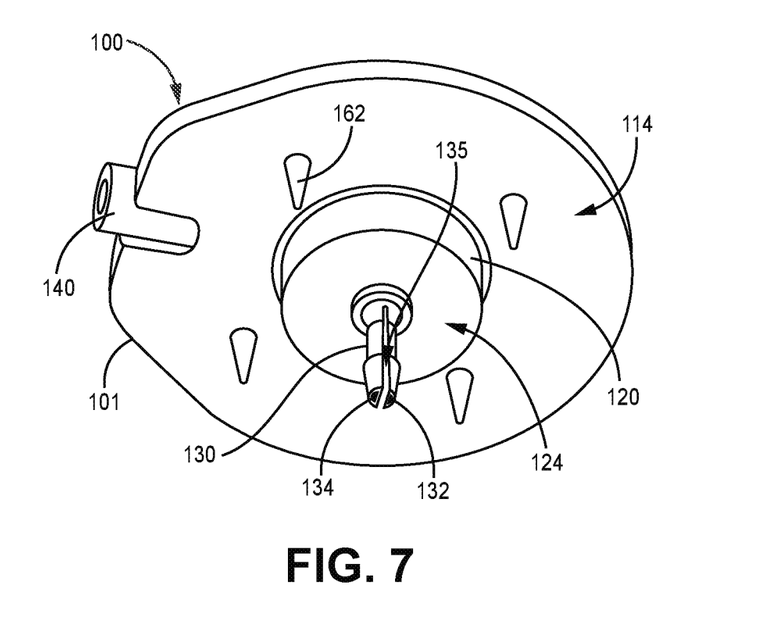
FIG. 7 is a schematic perspective view showing a bottom of an embodiment of the implantable cranial medical device depicted in FIGS. 4-6.
Figure 8:
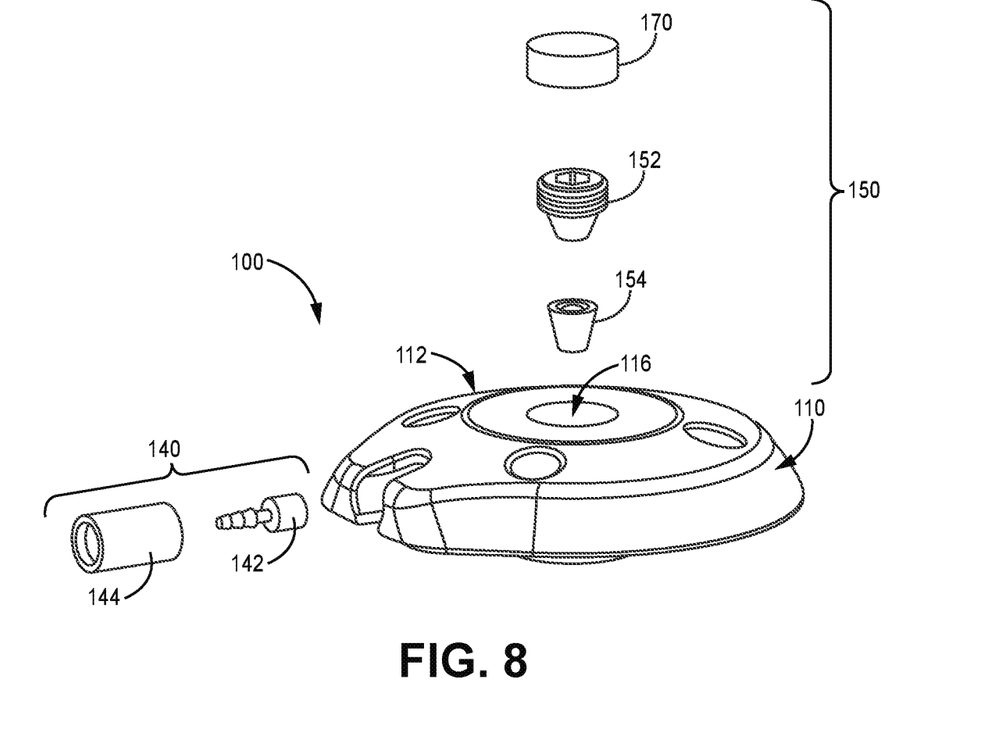
FIG. 8 is an exploded perspective view of an embodiment of an implantable cranial medical device showing components of a port and an external catheter connector.
Figure 9:
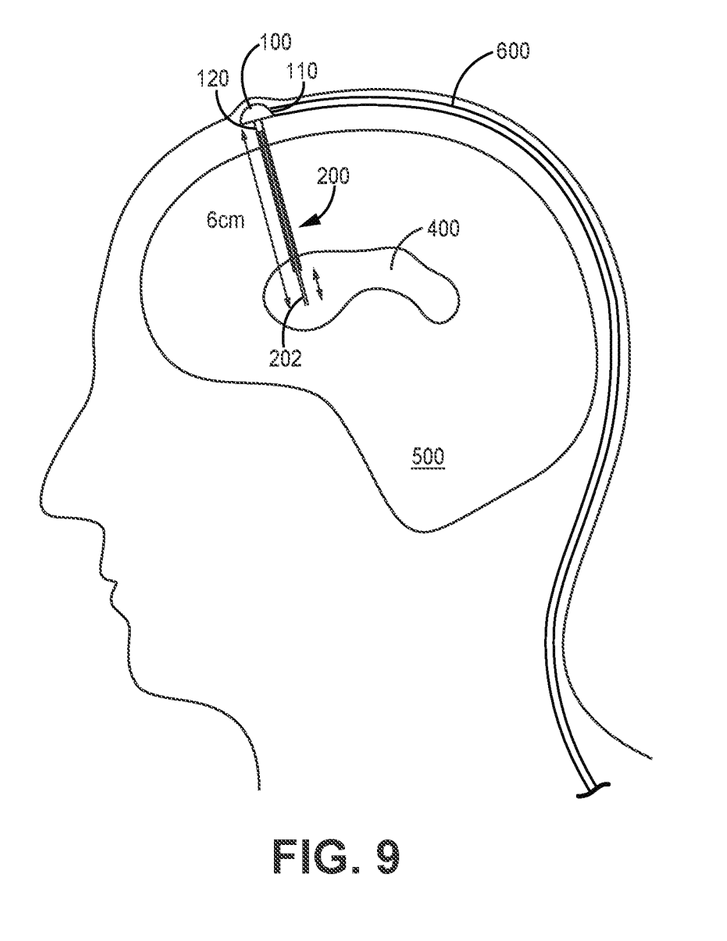
FIG. 9 is a schematic sectional view illustrating an embodiment of an implantable cranial medical device, CSF catheter, and accessory device catheter implanted in a patient.

As shown in FIG. 7, the CSF catheter connector 130 may include a slot 135 configured to receive a portion of a catheter that separates one lumen from another in a dual catheter. For example and with reference to FIG. 3, a central portion 215 of a body 210 of a CSF catheter 200 that separates a first lumen 212 from a second lumen 214 may be inserted into slot 135 of the CSF catheter connector 130 such that the first lumen 212 of the catheter 200 is placed in fluid communication with the first lumen 132 of the catheter connector 130 and such that the second lumen 214 of the catheter 200 is placed in fluid communication with the second lumen 134 of the catheter connector 130.

Referring now to FIG. 13, components of an accessory device catheter connector 140 and a port 150 associated with an upper flange portion 110 of an implantable medical device 100 are shown. The outer edge of the port 150 is defined by a first inlet 116 defined by a top surface 112 of the upper flange portion 110. The port 150 includes a septum 170 or cap, a compression wedge 152, and an axial ferrule 715, which defines a decreasing inner diameter moving in a direction from the top surface 112 of the upper flange portion 110 towards the bottom surface of the upper flange portion 110. The axial ferrule 715 serves to guide a needle inserted into the port 150 into a position suitable for placing a lumen of the needle in fluid communication with the first fluid path of the device 100. The axial ferrule 715 may also limit insertion of the needle beyond a bottom end of the ferrule 715.

The accessory device catheter connector 140 includes a compression fitting, such as sleeve 144, defining a lumen configured to receive an accessory device catheter and a barbed fitting 142 configured to be inserted into a lumen of the accessory device catheter. The barbed fitting 142 includes a passageway in communication with the second fluid path of the device 100. The compression sleeve 144 may be disposed about the accessory device catheter and slid towards the end of the catheter after the catheter has been advanced over the barbed fitting 142 to cause the external catheter to be compressed against the barbed fitting 144.

As shown in FIG. 16, a distal end portion 202 of a CSF catheter 200 may be implanted in a lateral ventricle 400 of a brain 500 of a subject. The proximal end of the CSF catheter 200 may be coupled to a CSF catheter connector (not shown) of the device 100. Alternatively, the catheter 200 may be a part of the device 100. The lower portion 120 of the implantable cranial medical device 100 may be positioned within a burr hole (not shown) of a skull (not shown) of the subject, and the upper flange portion 110 of the device 100 may be implanted between the skull and the scalp of the subject. An accessory device catheter 600 may be coupled to an accessory device catheter connector (not shown) of the implantable cranial medical device 100 and positioned along the skull of the subjected and tunneled to a position in the patient remote from the implantable medical device 100. For example, the accessory device catheter 600 may be operably coupled to an infusion device implanted subcutaneously in a location of a torso, such as in the abdominal region, of the subject.

The CSF catheter 300 may have any suitable length, such as about 6 centimeters to about 7 centimeters, which should be sufficient to connect to the implantable medical device 100 and extend into the lateral ventricle 400 of the brain 500 of the subject. If the CSF catheter is to be implanted in, for example, an intrathecal space in the spinal canal, the catheter is sufficiently long to extend from the location of the device to the CSF-containing area of the patient in which the distal end 202 is configured to be implanted.

The implantable medical devices and associated devices described herein may be used in any suitable mater. If the distal end portion of the CSF catheter is positioned in a CSF-containing space of the subject, the implantable medical device may be permit infusion of therapeutic fluid and aspiration of CSF through separate lumens of the CSF catheter or catheters and through separate fluid pathways of the device.

For example, fluid may be aspirated from the CSF-containing space of the subject through the first lumen of the CSF catheter and through the first fluid path of the implantable medical device. A lumen of a needle may be placed in communication with the first fluid path of the implantable medical device. For example, the needle may be inserted into the first inlet in communication with the first fluid pathway. The fluid may be aspirated from the CSF-containing space of the subject through lumen of the needle.

In some embodiments, the first fluid path of the implantable medical device and the first lumen of the CSF catheter may be used to infuse fluid, such as a fluid comprising a therapeutic agent, into the CSF-containing space of the subject. For example, a lumen of a needle may be placed in communication with the first fluid path of the implantable medical device. For example, the needle may be inserted into the first inlet in communication with the first fluid path. The fluid may be infused through the lumen of the needle, through the first fluid path of the implantable cranial medical device, and through the first lumen of the CSF catheter to the CSF-containing space of the subject.

A fluid may be infused to the CSF-containing space of the subject by infusing the fluid through the second flow path of the implantable medical device and through the second lumen of the CSF catheter. The fluid may comprise a therapeutic agent. An infusion device may be coupled to the second fluid path of the implantable medical device, such as via an accessory device catheter, and the fluid may be infused from the infusion device to the CSF-containing space. The infusion device may be an implanted infusion device.

By providing separate lumens and fluid paths, infusion and aspiration (or infusion) may be conducted simultaneously. Accordingly, infusion of a first therapeutic fluid does not need to be disrupted to aspirate a sample of CSF or to introduce a second therapeutic fluid to the CSF. Such lack of disruption of infusion of the first therapeutic fluid may provide for improved therapy.

The devices, kits, and systems described herein may extend the space and time a therapeutic agent is available to its brain target improving pharmacokinetics and pharmacodynamics of the therapeutic agent in the brain relative to prior approaches for direct infusion into the central nervous system.

CSF aspirated via the first fluid path may be used for any suitable purpose. For example, aspirated CSF may be used to determine the concentration of a therapeutic agent, which may be introduced via a therapeutic fluid infused through the second fluid path to the CSF. The flow rate or pattern of infused therapeutic may be adjusted based on concentrations of therapeutic agent determined to be present in the aspirated CSF.

The aspirated CSF may be used to determine whether the subject may have an infection due to implantation or use of the implantable cranial medical device and associated devices. If, for example, infectious bacteria, fungi, or viruses are detected in the aspirated CSF, antibiotics, anti-fungal agents, or antiviral agents may be administered to the CSF through, for example the first fluid flow path of the cranial medical device and first lumen of the CSF catheter. Concentration or presence of infectious pathogens in subsequently aspirated CSF may be used to determine whether parameters of therapy should be adjusted or whether the medical device and associated devices should be explanted.

The aspirated CSF may be used to detect or diagnose serious bacterial, fungal and viral infections, including meningitis, encephalitis and syphilis. The aspirated CSF may be used to detect or diagnose bleeding around the brain (subarachnoid hemorrhage). The aspirated CSF may be used to detect or diagnose certain cancers involving the brain or spinal cord. The aspirated CSF may be used to detect or diagnose certain inflammatory conditions of the nervous system, such as multiple sclerosis and Guillain-Barre syndrome.

For example, normal CSF white blood cell count is between 0 and 5, and normal CSF red blood cell count is 0. An increase of white blood cells may indicate infection or inflammation, an increase in red blood cell count may indicate bleeding into the cerebrospinal fluid.

The aspirated CSF may be used to determine whether the presence or concentration of a biological marker associated with the disease being treated changes in response to the infused therapeutic fluid. In fact, all diseases of the central nervous system have a CSF profile that is unique to the disease and to the progression of the disease.

SUMMARY OF SOME SELECTED ASPECTS

Various aspects of implantable cranial medical devices, systems and kits including implantable cranial medical devices, methods for implanting implantable cranial medical devices and associated devices, and methods for using implantable cranial medical devices and associated devices are discloses herein. A summary of some of the aspect is provided below.

In a first aspect, an implantable medical device for withdrawing cerebrospinal fluid (CSF) from a CSF-containing space of a subject and for infusing fluid into the subject comprises a first inlet configured to be accessed by a needle of an aspiration device; a first outlet; a first fluid pathway extending from the first inlet to the first outlet; a second inlet; a second outlet; a second fluid pathway extending from the second inlet to the second outlet; and one or more CSF catheters comprising a first lumen, a first distal opening in fluid communication with the first lumen, a second lumen and a second distal opening in fluid communication with the second lumen. The first lumen is in fluid communication with, or is configured to be placed in fluid communication with the first fluid pathway. The second lumen is in fluid communication with, or is configured to be placed in fluid communication with the second fluid pathway. The first distal opening is configured to be placed in the CSF-containing space of the subject. The first fluid pathway is free of a filter configured to prevent passage of a microbe.

A second aspect is an implantable medical device of the first aspect, wherein the second fluid pathway comprises a filter configured to allow passage of a therapeutic fluid and configured to prevent passage of a microbe.

A third aspect is an implantable medical device of the first of second aspect, wherein the second distal opening is configured to be placed in the CSF-containing space.

A fourth aspect is an implantable medical device of any one of aspects 1 to 3, comprising a self-sealing septum, wherein the septum is positioned across the first inlet.

A fifth aspect is an implantable medical device of any one of the first four aspects, wherein the device comprises a top surface, and wherein the top surface comprises the first inlet.

A sixth aspect is an implantable medical device of any one of aspects 1 to 5, wherein the device comprises a side surface, wherein the side surface comprises the second inlet.

A seventh aspect is an implantable medical device of any one of aspects 1 to 6, wherein the second inlet is configured to be coupled to an accessory device catheter.

An eighth aspect is an implantable medical device of any one of aspects 1 to 7, wherein the first and second inlets are configured to be positioned in proximity to a skull.

A ninth aspect is an implantable medical device of any one of aspects 1 to 8, wherein at least a portion of the device is configured to be positioned in or around a burr hole in a skull.

In a tenth aspect, a method comprises implanting the device of any one of aspects 1 to 9 in the subject; aspirating CSF from the subject through the first distal opening, the first lumen, and the first fluid pathway; and infusing a therapeutic fluid to the subject through the second fluid pathway, the second lumen, and the second distal opening.

All scientific and technical terms used herein have meanings commonly used in the art unless otherwise specified. The definitions provided herein are to facilitate understanding of certain terms used frequently herein and are not meant to limit the scope of the present disclosure.

As used herein, singular forms "a," "an" and "the" include plural referents unless the context clearly dictates otherwise. As used in this specification and the appended claims, the term "or" is generally employed in its sense including "and/or" unless the content clearly dictates otherwise. The term "and/or" means one or all of the listed elements or a combination of any two or more of the listed elements.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful and is not intended to exclude other embodiments from the scope of the inventive technology.

Any direction referred to herein, such as "top," "bottom," "side," "upper," "lower," and other directions or orientations are described herein for clarity and brevity but are not intended to be limiting of an actual device or system. Devices and systems described herein may be used in a number of directions and orientations.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that any particular order be inferred. Any recited single or multiple feature or aspect in any one claim can be combined or permuted with any other recited feature or aspect in any other claim or claims.

The headings used herein are for organizational purposes only and are not meant to be used to limit the scope of the description. As used throughout this application, the word "may" is used in a permissive sense (i.e., meaning having the potential to), rather than the mandatory sense (i.e., meaning must).

The words "include," "including," and "includes" indicate open-ended relationships and therefore mean including, but not limited to. Similarly, the words "have," "having," and "has" also indicated open-ended relationships, and thus mean having, but not limited to. Similarly, the terms "comprise" and "comprising" indicate open-ended relationships, and thus mean comprising, but not limited to. The terms "consisting essentially of" and "consisting of" are subsumed within the term "comprising." For example, a catheter comprising tubing may be a catheter consisting of tubing. The term "consisting essentially of" means a recited list of one or more items belonging to an article, kit, system, or method and other non-listed items that do not materially affect the properties of the article, kit, system, or method.

The terms "first," "second," "third," and so forth as used herein are used as labels for nouns that they precede, and do not imply any type of ordering (e.g., spatial, temporal, logical, etc.) unless such an ordering is otherwise explicitly indicated. For example, a "second" feature does not require that a "first" feature be implemented prior to the "second" feature, unless otherwise specified. A "second" feature does not necessarily require or imply that a "first" feature is needed or present.

Various components may be described as "configured to" perform a task or tasks. In such contexts, "configured to" is a broad recitation generally meaning "having structure that" performs the task or tasks during operation. As such, the component can be configured to perform the task even when the component is not currently performing that task (e.g., a catheter connector may be configured to place a lumen of a catheter in fluid communication with a fluid path, even when the catheter is not connected to the catheter connector).

Various components may be described as performing a task or tasks, for convenience in the description. Such descriptions should be interpreted as including the phrase "configured to." Reciting a component that is configured to perform one or more tasks is expressly intended not to invoke 35 U.S.C. § 112 paragraph (f), interpretation for that component It will be apparent to those skilled in the art that various modifications and variations can be made to the present inventive technology without departing from the spirit and scope of the disclosure. Since modifications, combinations, sub-combinations and variations of the disclosed embodiments incorporating the spirit and substance of the inventive technology may occur to persons skilled in the art, the inventive technology should be construed to include everything within the scope of the appended claims and their equivalents.

What is claimed is:

1. An implantable medical device for withdrawing cerebrospinal fluid (CSF) from a CSF-containing space of a subject and for infusing fluid into the subject, the device comprising: a first inlet configured to be accessed by a needle of an aspiration device; a first outlet; a first fluid pathway extending from the first inlet to the first outlet; a second inlet configured to be accessed by a needle of an infusion device and to be inaccessible by the needle of the aspiration device; a second outlet; a second fluid pathway extending from the second inlet to the second outlet; and one or more CSF catheters comprising a first lumen, a first distal opening in fluid communication with the first lumen, a second lumen and a second distal opening in fluid communication with the second lumen, wherein the first lumen is in fluid communication with, or is configured to be placed in fluid communication with the first fluid pathway, wherein the second lumen is in fluid communication with, or is configured to be placed in fluid communication with the second fluid pathway, wherein the first distal opening is configured to be placed in the CSF-containing space of the subject, and wherein the first fluid pathway is free of a filter configured to prevent passage of a microbe.

2. The implantable medical device of claim 1, wherein the first inlet is configured to be inaccessible by the needle of the infusion device.

3. The implantable medical device of claim 1, wherein the second fluid pathway comprises a filter configured to allow passage of a therapeutic fluid and configured to prevent passage of a microbe.

4. The implantable medical device of claim 3, wherein the second distal opening is configured to be placed in the CSF-containing space.

5. The implantable medical device of claim 4, comprising a self-sealing septum, wherein the septum is positioned across the first inlet.

6. The implantable medical device of claim 5, wherein the device comprises a top surface, and wherein the top surface comprises the first inlet.

7. The implantable medical device of claim 6, wherein the device comprises a side surface, wherein the side surface comprises the second inlet.

8. The implantable medical device of claim 7, wherein the second inlet is configured to be coupled to an accessory device catheter.

9. The implantable medical device of claim 1, wherein the second distal opening is configured to be placed in the CSF-containing space.

10. The implantable medical device of claim 1, wherein the device comprises a side surface, wherein the side surface comprises the second inlet.

11. The implantable medical device of claim 1, wherein the second inlet is configured to be coupled to an accessory device catheter.

* * * * *